US00PP30978P3

(12) United States Plant Patent
Elliott et al.

(10) Patent No.: US PP30,978 P3
(45) Date of Patent: Oct. 29, 2019

(54) APPLE TREE NAMED 'HONEYSUCKLE ROSE #1-6'

(50) Latin Name: *Malus domestica*
Varietal Denomination: Honeysuckle Rose #1-6

(71) Applicant: Stark Bro's Nurseries & Orchards Co., Louisiana, MO (US)

(72) Inventors: Lee Elliott, Winchester, IL (US); Mary Elliott, Winchester, IL (US)

( * ) Notice: Subject to any disclaimer, the term of this patent is extended or adjusted under 35 U.S.C. 154(b) by 0 days.

(21) Appl. No.: 15/932,500

(22) Filed: Mar. 7, 2018

(65) Prior Publication Data

US 2019/0281739 P1 Sep. 12, 2019

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Sandberg Phoenix & von Gontard P.C.

(57) ABSTRACT

'Honeysuckle Rose #1-6' is a new variety derived from 'Simmons Gala' characterized by a unique red tint extending into the flesh and a combination of crispness, a thick fruit skin, long stem, resistance to early fruit drop, resistance to fire blight, and late ripening.

10 Drawing Sheets

Latin name: *Malus domestica.*
Varietal denomination: 'Honeysuckle Rose #1-6'.

CROSS-REFERENCES TO RELATED APPLICATIONS not applicable

BACKGROUND OF THE INVENTION

1. Field of Invention

'Honeysuckle Rose #1-6' is a new and distinct variety of apple tree (*Malus domestica*).

2. Description of the Related Art

The new variety was selected from a population of seedlings derived from crossing the apple varieties 'Simmons Gala' (U.S. Plant Pat. No. 10,840), a/k/a 'Buckeye Gala®', male parent, and 'Honeycrisp' (U.S. Plant Pat. No. 7,197), female parent, on April 1998 in trees in Winchester, Ill. 'Honeysuckle Rose #1-6' has been asexually reproduced through succeeding asexual propagation also in Winchester, Ill. Examination of the various trees of the cultivar has confirmed that the combination of characteristics described herein are firmly fixed through successive generations.

The seedling tree was grown to the $90^{th}$ node in 2000. The apex scion was removed and limb grafted to limbs of existing 10-year-old 'Red Delicious' (unpatented) apple trees on 'EMLA 7' (unpatented) rootstocks. Fruiting occurred in 2003, was determined to be unique in outstanding flavor and texture. 20 new trees were grafted in 2004 using 'Budagovsky 9' (Bud 9) (unpatented) and 'EMLA 26' (unpatented) rootstocks. All the new trees stayed true to form as the seedling tree and limb grafts.

Texture, flavor, and appearance of the 'Honeysuckle Rose #1-6' fruit are unique and dissimilar from the parent trees.

Uniquely, a red tint extends 2-5 mm into the flesh of the fruit. The combined traits inherited are good qualities, such as a texture and crispness similar to 'Honeycrisp' with a thicker fruit skin, longer stem, tree habit, and resistance to early fruit drop similar to 'Simmons Gala'. The tree has been observed to have better fire blight resistance than either of its parents. Also, 'Honeysuckle Rose #1-6' ripens 3 weeks later than either of its parents.

The newly disclosed and distinct variety/cultivar annually produces fruit that is normally ripe for harvesting and shipping on or about October 1 through October 10 under the ecological and climatological conditions prevailing around approximately the area of Winchester, Ill. The fruit is most notable for its use as a fresh-eating/dessert apple that may also be used for cooking and juicing. The fruit is sub-acid-to-sweet with high brix.

The present variety produces large-sized pome. The fruit is typically cherry-red over yellow in color when ripe, depending on maturity and location in the tree. The flesh of the fruit is creamy white when ripe.

PHOTOGRAPHS ACCOMPANYING SUBMISSION

The photographs submitted herewith show the color of our new variety/cultivar as nearly as reasonably possible to make the same in a color illustration of this character:

DESCRIPTION OF THE NEW CULTIVAR

Figure 1:
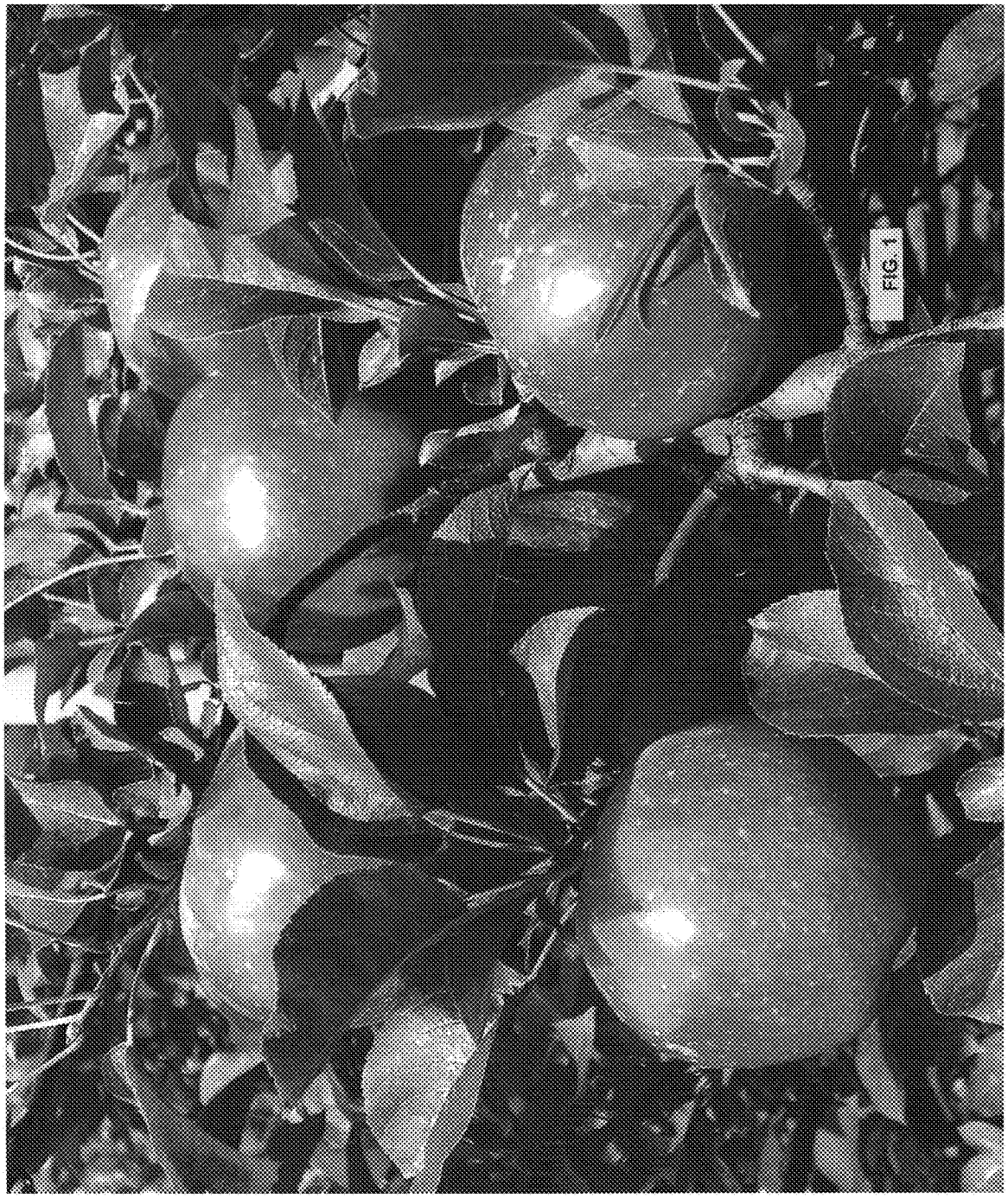
FIG. 1 is a photograph of the fruit of the new and distinct variety apple tree 'Honeysuckle Rose #1-6 Apple' described in the below botanical description at six years.
Figure 2:
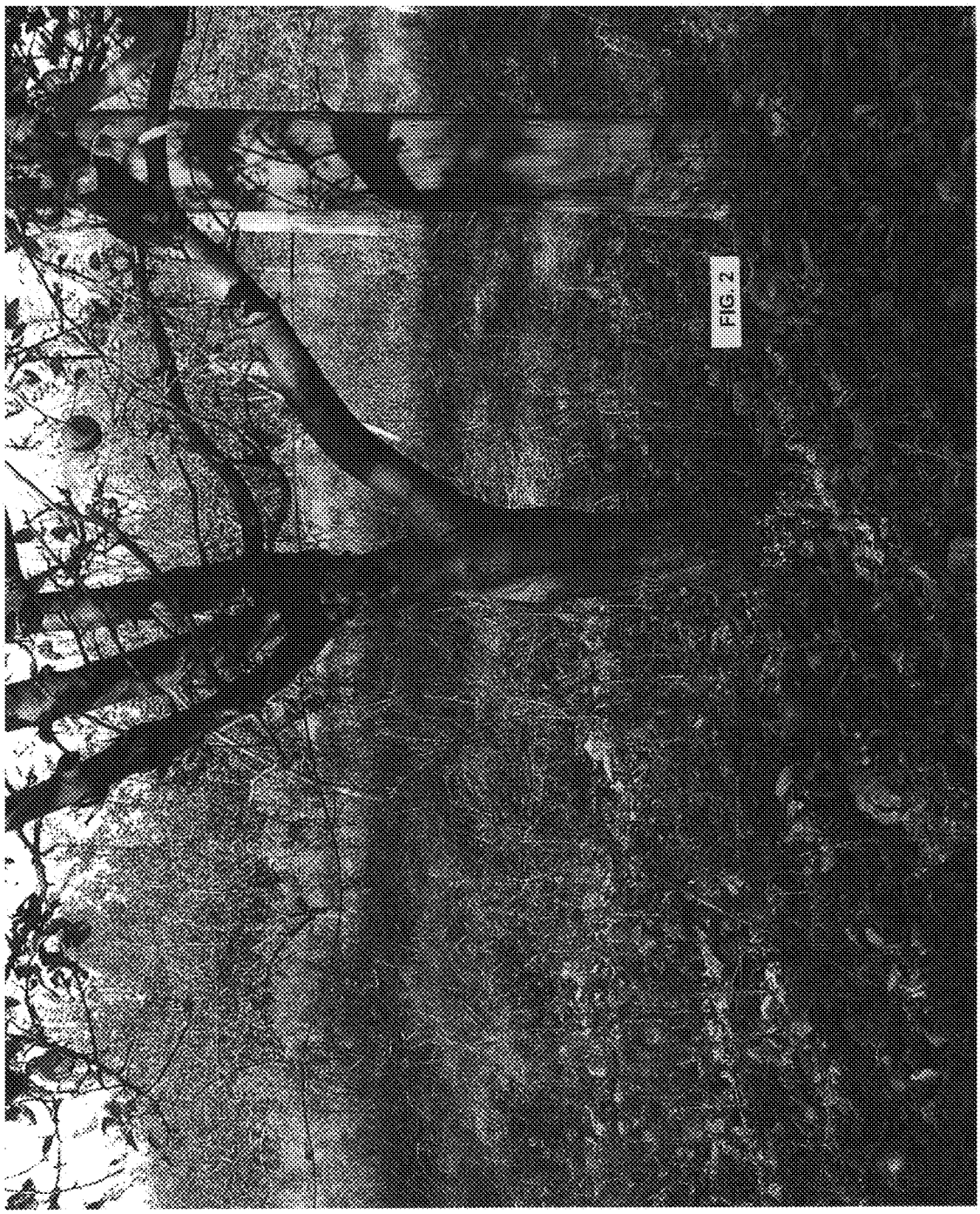
FIG. 2 is a photograph of the trunk and limb habit of the tree.
Figure 3:
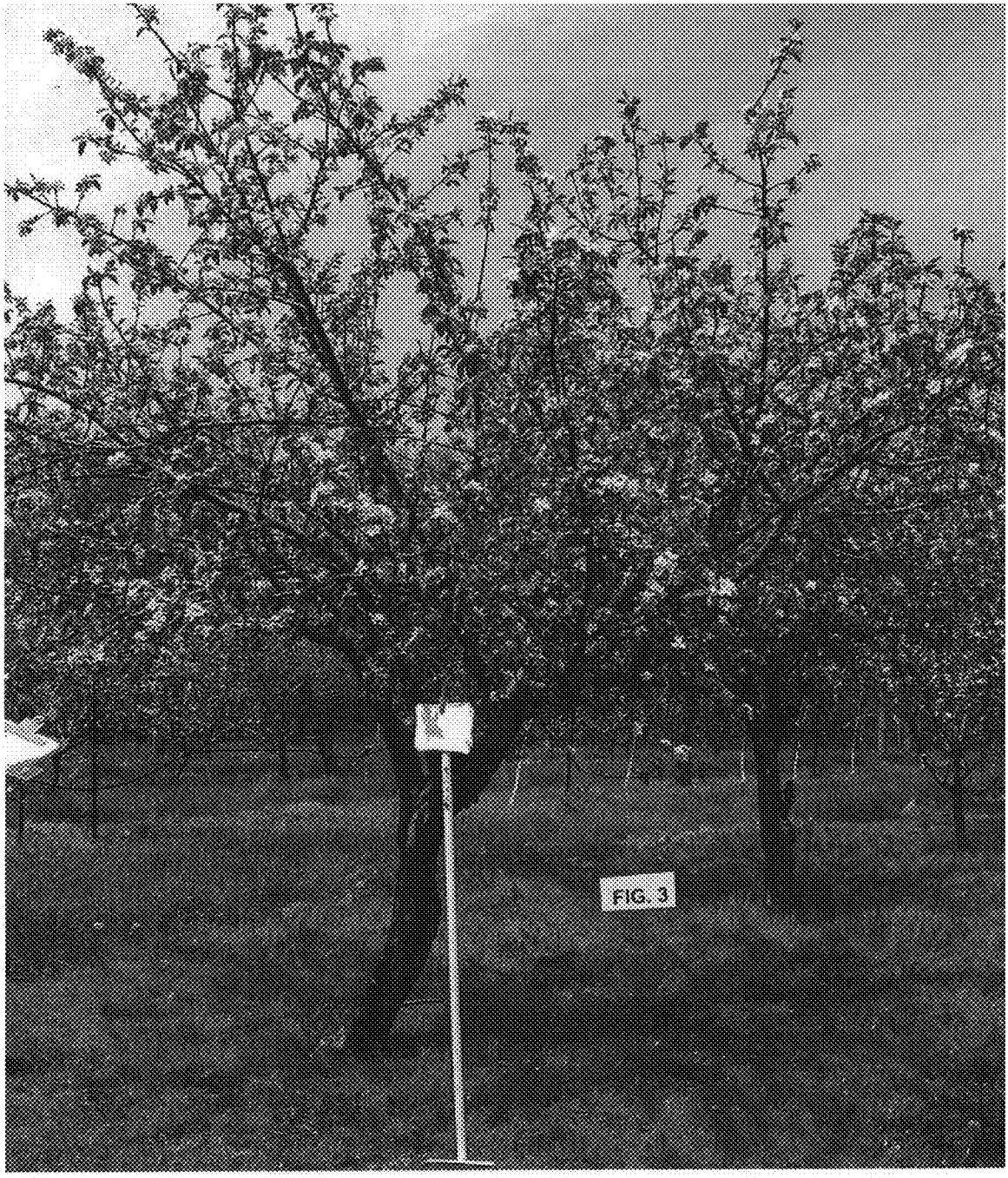
FIG. 3 is a photograph of the blossoms and limb habit of the tree.
Figure 4:
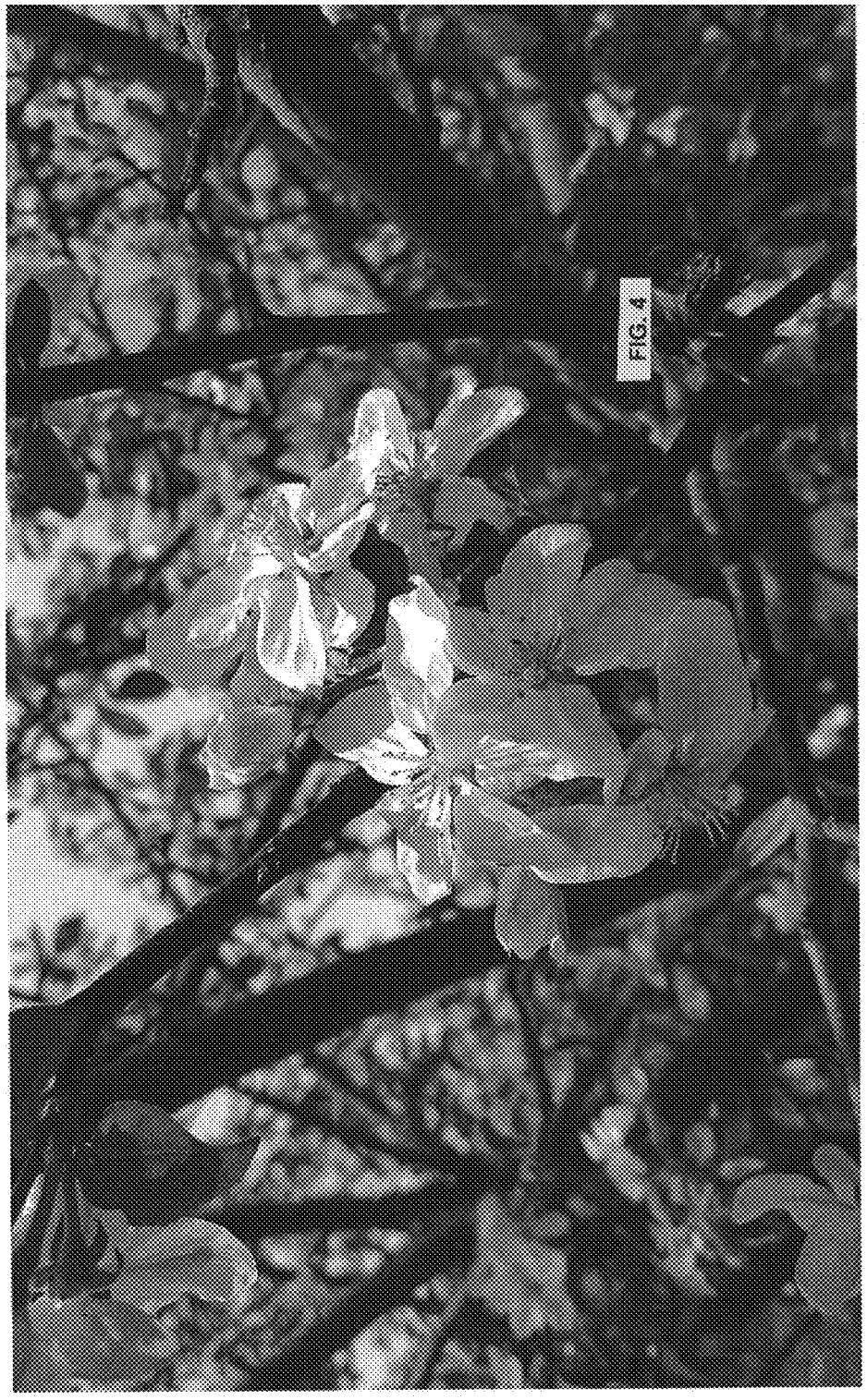
FIG. 4 is a photograph of the open blossoms of the tree.
Figure 5:
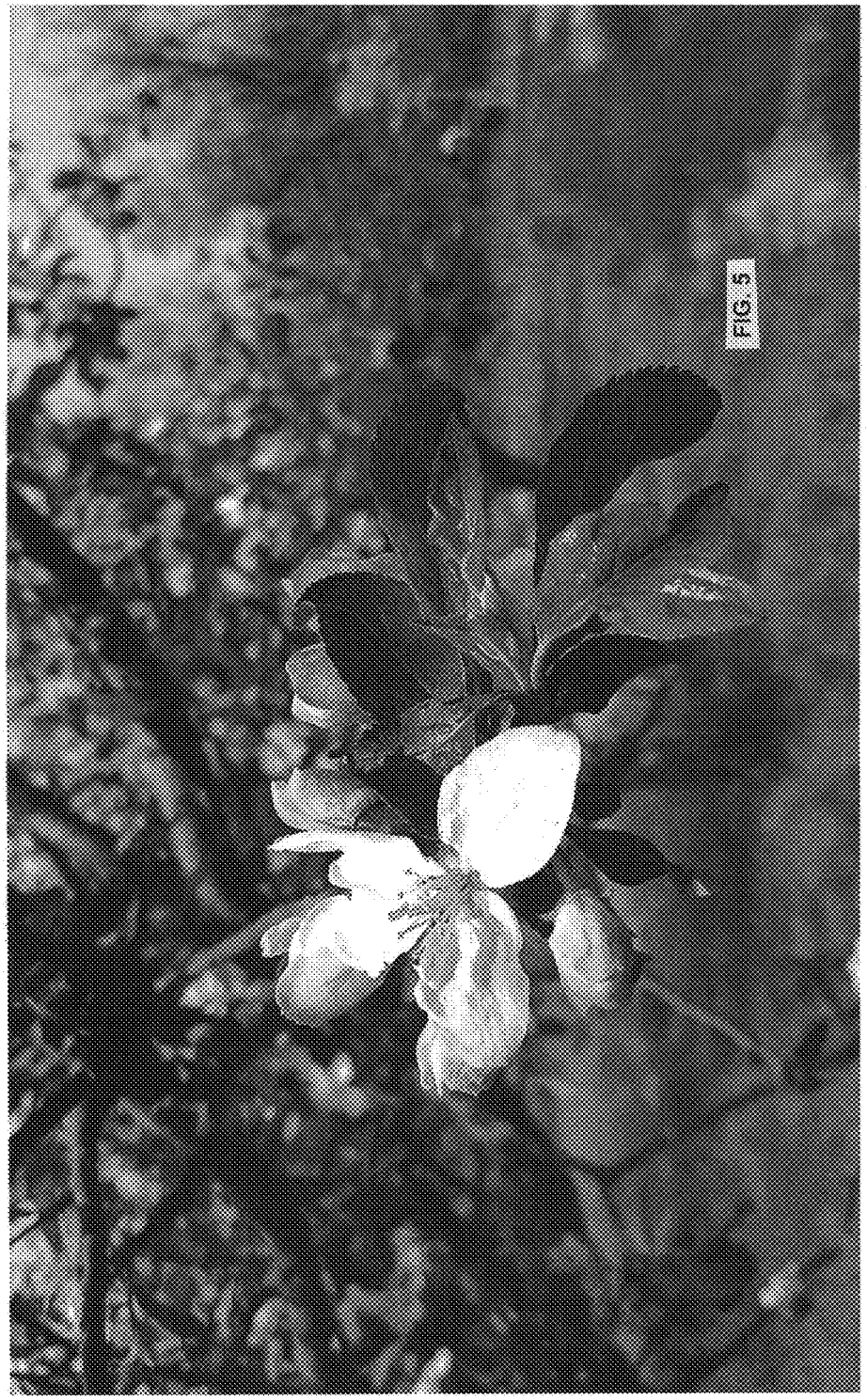
FIG. 5 is a photograph of the closed blossoms of the tree.
Figure 6:
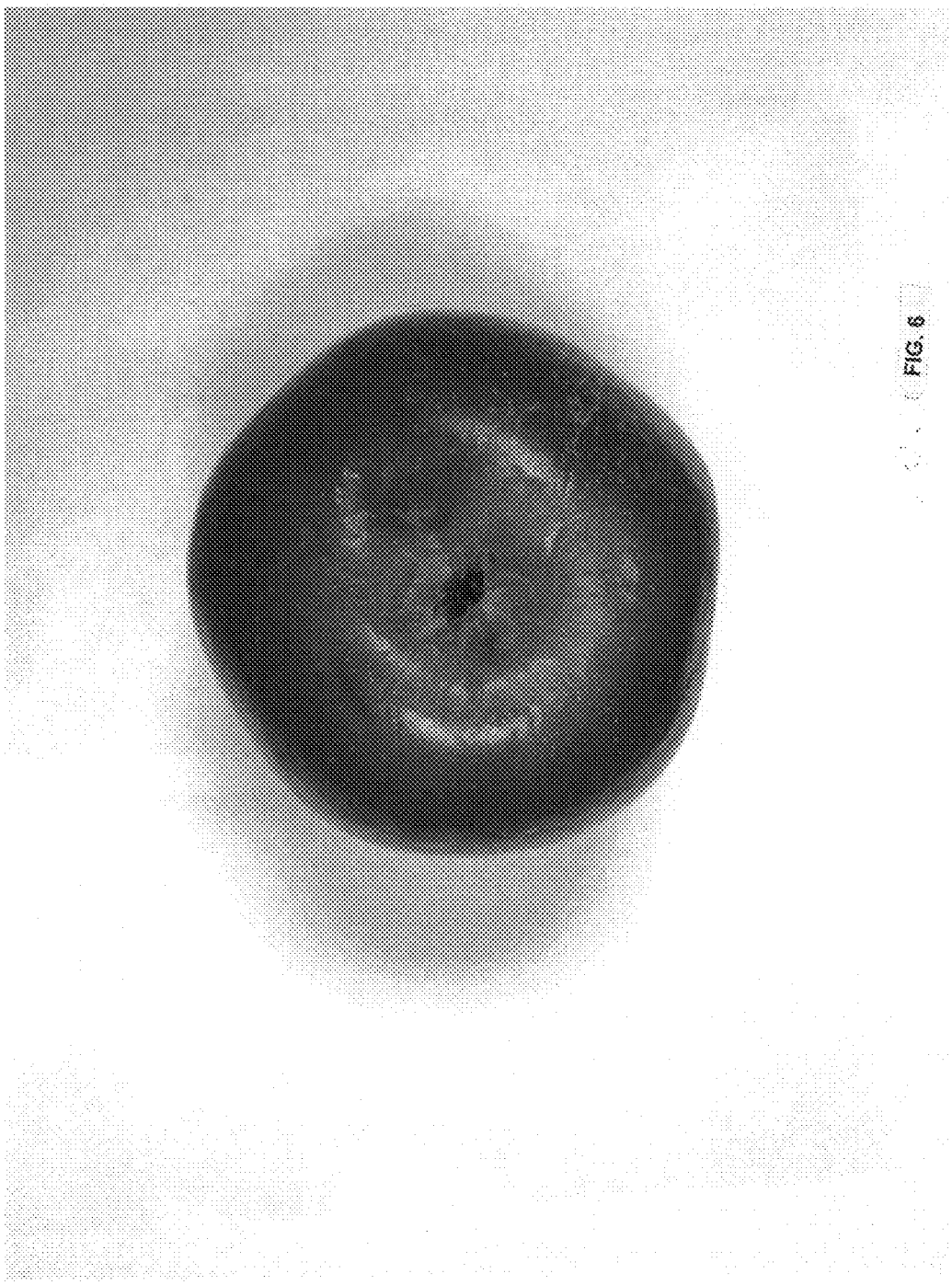
FIG. 6 is a photograph of the 'Honeysuckle Rose #1-6' fruit bottom.
Figure 7:
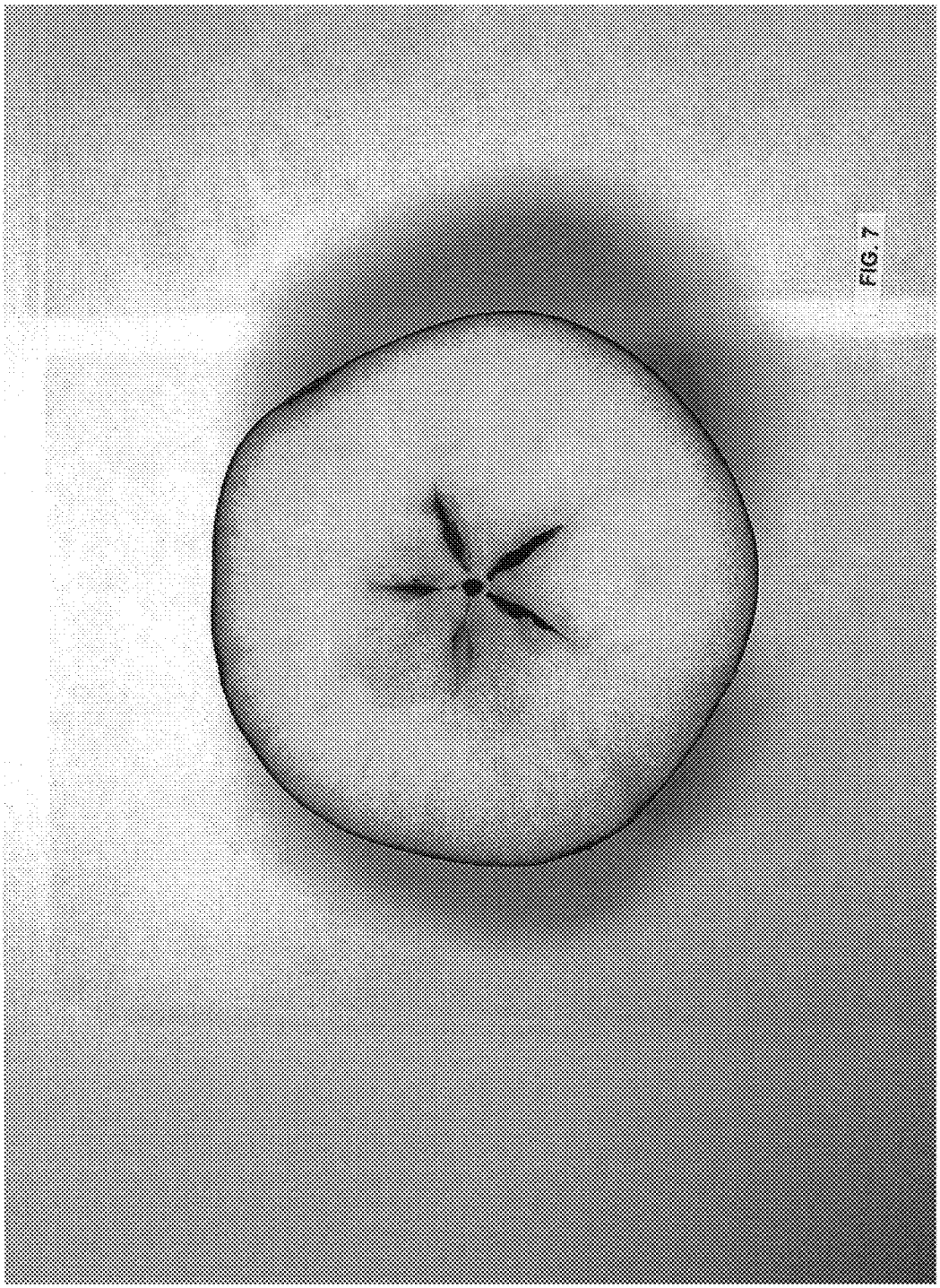
FIG. 7 is a photograph of the 'Honeysuckle Rose #1-6' fruit cut in half.
Figure 8:
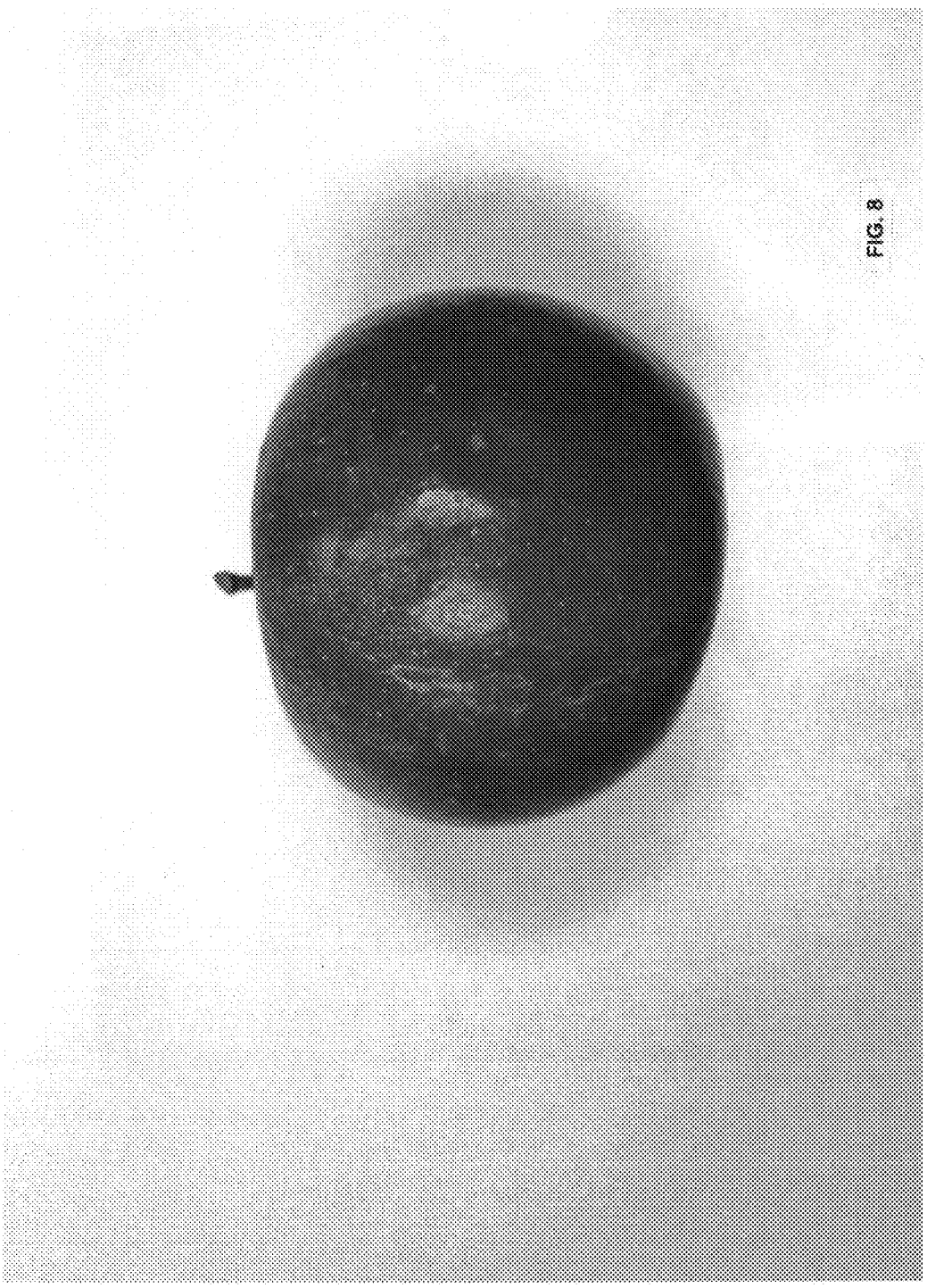
FIG. 8 is a photograph of the 'Honeysuckle Rose #1-6' fruit side.
Figure 9:
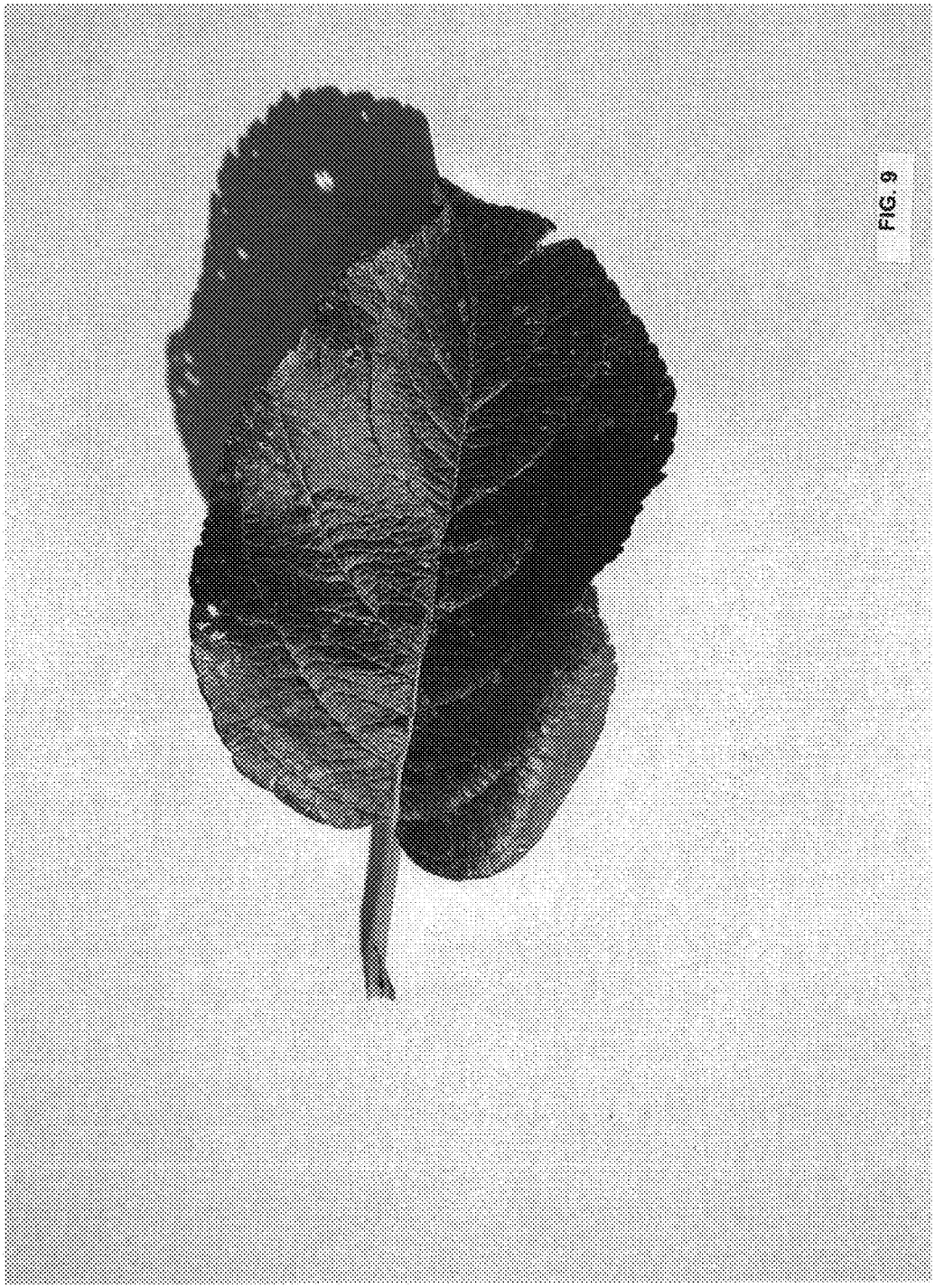
FIG. 9 is a photograph of the tree's leaf top surface.
Figure 10:
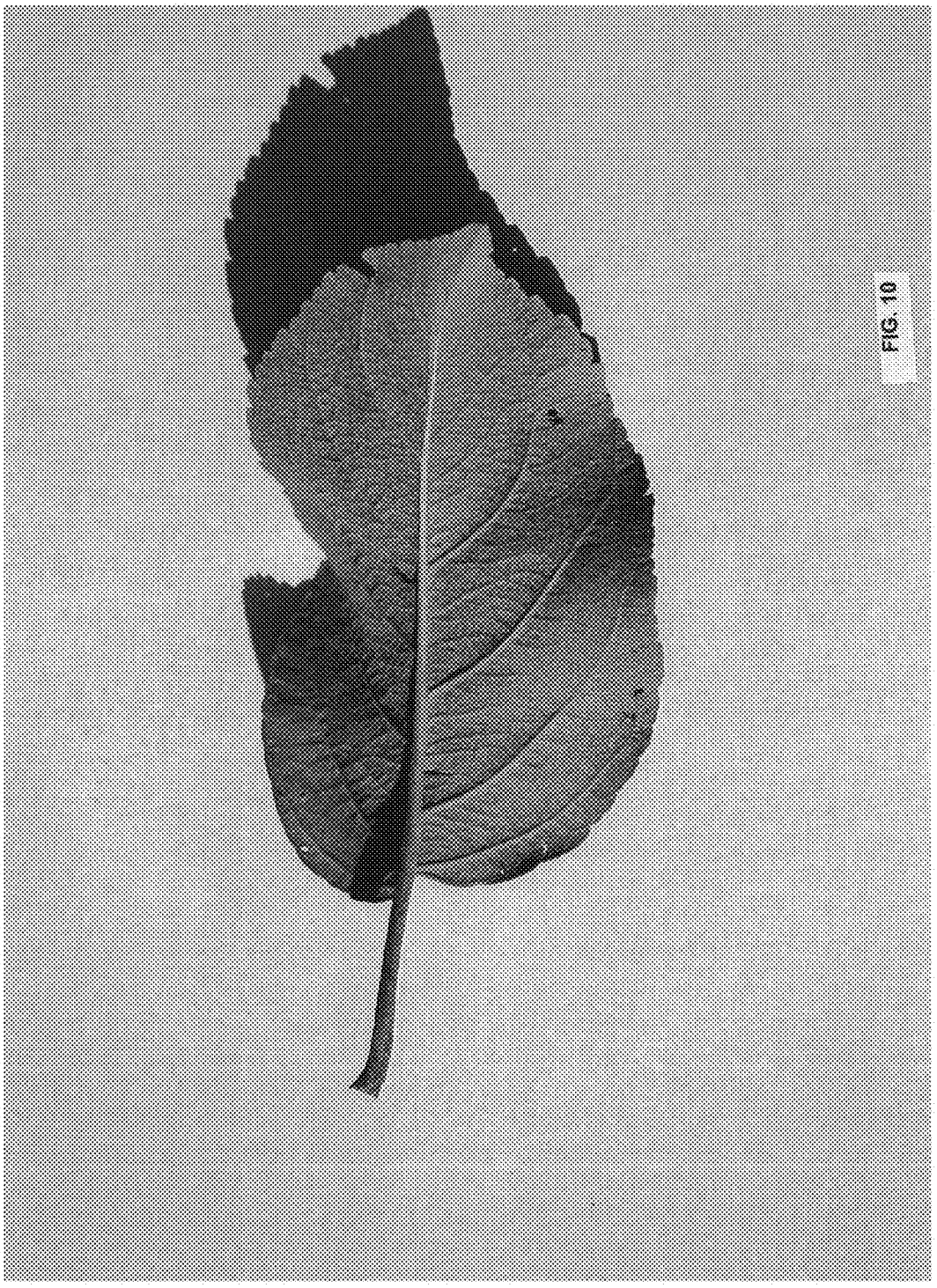
FIG. 10 is a photograph of the tree's leaf bottom surface.

The following is a detailed description of our new cultivar of apple tree 'Honeysuckle Rose #1-6' with color terminology in accordance with The Royal Horticulture Society (R.H.S.) Colour Chart, except where the context indicates a term having its ordinary dictionary meaning. Our new tree has not been observed under all growing conditions and variations may occur as a result of different growing conditions. All progeny of our new variety of 'Honeysuckle Rose #1-6' Apple Tree, insofar as have been observed, have been identical in all the characteristics described below.

Other than as set forth herein, as of this time, no other characteristics of our new 'Honeysuckle Rose #1-6' Apple Tree have been observed by the inventors which are different from the characteristics common to apple trees.

Parentage: A cross between 'Simmons Gala' (U.S. Plant Pat. No. 10,840), male parent and 'Honeycrisp', female parent (U.S. Plant Pat. No. 7,197) made in April 1998.

Locality where grown and observed: Winchester, Ill.

Tree:

*Size.*—3.7-4.8 meters.

*Vigor.*—Medium vigor on larger rootstocks like 'EMLA 26', less vigorous on M9 or B9.

*Tree form.*—Open and spreading.

*Tree height.*—6 meters.

*Tree crown.*—Width: 6.71 meters.

*Productivity.*—Reliably productive tree; may overset if not thinned.

*Regularity of bearing.*—Bears annually.

*Trunk diameter.*—16.51 centimeters at 1-meter height.

Bark:

*Surface texture.*—Grainy with rough lenticels.

*Bark color.*—Greyed Green (Fan #4, Sheet 197-B).

*Bark lenticels.*—

*Numbers.*—Numerous; approximately 8 per centimeter area.

*Lenticels.*—Shape — Elongated.

*Lenticels.*—Size — 2 to 5 millimeters.

*Lenticels.*—Color — Greyed Orange (Fan #4, Sheet 164-C).

Branches:

*Size.*—Normal in diameter for the species. Approximately 7.62 centimeters around with a 3.7-meter length.

*Surface texture.*—Fairly smooth.

*Lenticels.*—Fairly rough.

*Upper branches.*—Size — 3.81 centimeters with a 1.83-meter length.

*Surface texture.*—Older branches — Slightly rough.

*Older branches.*—Color — Greyed Green (Fan #4, Sheet 198-A).

*One-year-old shoots and spurs.*—Color — Greyed Green (Fan #4, Sheet 200-D).

*Current season's shoots.*—Color — Brown (Fan #4, Sheet 144-B).

*Actively growing shoots.*—Color — Yellow Green (Fan #3, Sheet 144-B).

*Expanding shoot tips and young leaves.*—Color — Yellow Green (Fan #3, Sheet 144-A).

*Internode length.*—Approximately 3 to 4.5 centimeters between adjacent nodes.

Leaves:

*Size.*—Generally — Ovate to oblong.

*Leaf length.*—Approximately 6.5 to 7.0 centimeters not including petiole.

*Leaf width.*—Approximately 5.3 to 6.3 centimeters.

*Leaf thickness.*—0.1 millimeter to 0.2 millimeter.

*Mature leaf texture.*—Pubescence on bottom (lamina); smooth with prominent veins.

*Leaf form.*—Generally — Oblong to ovate.

*Leaf apices.*—Shape — Pointed, sharp.

*Leaf surface.*—Texture — Smooth, grainy, rough.

*Leaf color.*—Mature leaves — Upper surface Dark Green (Fan #3, Sheet 137-C); Lower surface lighter Green (Fan #3, Sheet 138-B).

*Color.*—Mid-Vein — Pale Yellow-Green (Fan #3, Sheet 139-D).

*Leaf margins.*—Generally — Serrate to crenate.

*Serrations.*—Size — Height is 0.1 centimeter and 0.2 to 0.4 centimeters apart.

*Leaf margins.*—Shape — Slightly undulate.

*Leaf petiole.*—Size — Average, with a length of about 3.3 to 3.8 centimeters.

*Petiole base.*—Shape — Flattened.

*Petiole.*—Color — Yellow-Green on younger leaves (Fan #3, Sheet 139-C).

*Petiole.*—Surface texture — Moderately smooth.

*Immature leaves.*—Surface texture — Thick pubescence on bottom, lamina being smooth and shiny.

*Leaf stipules.*—Generally — About 0.75 to 1.3 millimeter in width.

*Leaf stipules.*—Form — Oblong, thin.

Flowers: Buds are considered relatively free from the bearing stem and are considered hardy under Winchester, Ill. climatic conditions.

*Flower buds.*—Shape — Clavate.

*Flower buds.*—Size — 1 centimeter.

*Flower buds.*—Color — Red (Fan #2, Sheet 63-B).

*Flower buds.*—Surface texture — Glabrate.

*Bloom time.*—Generally — Early to mid-April with many other apple varieties growing at the same geographic location.

*Date of full bloom.*—Observed at Winchester, Ill. on Apr. 18, 2016.

*Duration of bloom.*—Approximately 10 days; however, the date and duration of bloom can be substantially affected by the amount of chilling hours that occur during a given year, and the geographical location where the variety is grown.

*Flower size.*—Generally — Diameter — approximately 40-50 mm; height — approximately 16 mm.

*Bloom quantity.*—5.

*Flowers per node.*—As many as 5 can be produced.

*Petal numbers.*—5.

*Petal form.*—Ovate.

*Petal color.*—White (Fan #1, Sheet 36-D).

*Petal claw.*—Shape — Narrow to medium.

*Petal margins.*—Shape — Ruffled.

*Petal apices.*—Form — Somewhat rounded at tip.

*Flower pedicel.*—Size — Vary from 1.5 to 2 centimeters in length and from 1.5 to 2 centimeter thick.

*Flower pedicel*.—Color — Light Green (Fan #3, Sheet 144-D).
*Flower pedicel*.—Surface Texture — Light pubescent.
*Floral nectaries*.—Color — Yellow Green (Fan #3, Sheet 144-C).
*Calyx*.—Surface Texture — Slightly medium pubescent.
*Calyx*.—Color — Pale Green (Fan #3, Sheet 144-C).
*Sepals*.—Surface Texture — Medium pubescent.
*Sepals*.—Size — 6 millimeter.
*Sepals*.—Color — Pale Green (Fan #3, Sheet 144-C).
*Anthers*.—Size — 1.5 millimeter.
*Anthers*.—Color — Pale Yellow (Fan #1, Sheet 11-C).
*Pollen production*.—Abundant in quantity; heavy.
*Pollen*.—Color — Yellow (Fan #1, Sheet 11-B).
*Stamens*.—Color — White (Fan #1, Sheet 155-A).
*Pistil*.—Form — Uniform.
*Pistil*.—Length — 1 centimeter.
*Pistil*.—Surface Texture — Smooth.
*Pistil*.—Color — Pale Green (Fan #3, Sheet 144-D).

Fruit:

*Maturity when described*.—The fruit of the present variety of Honeysuckle Rose #1-6 apple tree is described at full commercial maturity hereinafter.
*Date of harvest*.—In 2013, the date of harvest was October 5. The date of harvest in 2014 was October 5. The date of harvesting is about October 5. The date of harvesting, noted above, are those that were observed at Winchester, Ill.
*Fruit size*.—Generally — Diameter was about 75 to 80 millimeters adjacent to the stem and about 65 to 70 millimeters around the base; Height was about 65 to 70 millimeters.
*Fruit form*.—Generally — Globose.
*Fruit symmetry*.—Somewhat variable, from fully symmetrical to slightly asymmetrical.
*Fruit stem*.—Size — Length dimension of about 18 to 20 millimeters and a thickness of about 1 to 1.5 millimeters.
*Fruit stem*.—Shape — Typically considered slightly curved.
*Fruit stem*.—Color — Light Green (Fan #4, Sheet 166-B).
*Fruit stem*.—Surface Texture — Moderately pubescent.
*Fruit lenticels*.—Color — Light Tan (Fan #4, Sheet 161-A).
*Stem cavity*.—Shape — Uniform and acute.
*Stem cavity*.—Size — Moderate; Width about 25 to 30 millimeters across the shoulders of the fruit; Depth about 8 to 10 millimeters.
*Fruit basin*.—Shape — Symmetrical; Approximately 2 millimeters in depth and 2.5 millimeters in breadth.
*Calyx*.—Form — Open.
*Core*.—Medium.
*Bundle area*.—Approximately 12 mm; oblate; symmetrical; acute at base.
*Bundle color*.—Light Green (Fan #3, Sheet 144-D).
*Core lines*.—Clasping; in-cross section indistinct.
*Carpellary area*.—Small; indistinct.
*Calyx tube*.—Glabrous toward base; funnel form.
*Stem of funnel*.—Long.
*Depth of tube to shoulder*.—Approximately 10 millimeters.
*Entire depth*.—Approximately 5 millimeters.
*Styles*.—Present; united toward base; pubescent toward base.
*Stamens*.—1 distinct whorl; median.
*Seed cells*.—Axile; closed.
*Cell walls*.—Thin; tough.
*Length*.—Approximately 46 millimeters.
*Breadth*.—Approximately 35 millimeters.
*Longitudinal section*.—Broadly ovate.
*Surface*.—Smooth.
*Cross-section*.—Narrow.
*Fruit carpels*.—Generally — 5 present and located within fruit core.
*Fruit carpels*.—Shape — Ovate long.
*Fruit carpel cells*.—Form — Generally closed although some open cells may be present.
*Fruit carpels*.—Surface Texture — Inner surface glabrous.
*Seeds*.—Numbers — Varies from 7 to as many as 10.
*Seeds*.—Size — Plump; length of 7 to 8 millimeters; width about 4 to 5 millimeters.
*Seeds*.—Thickness — Approximately 2.5 millimeters.
*Seed apex*.—Form — Acute.
*Seeds*.—Color — Dark Brown (Fan #4, Sheet 200-B). The color of the seeds at full commercial maturity is Brown (Fan #4, Sheet 200-A).
*Fruit skin*.—Thickness — Average.
*Fruit skin*.—Surface texture — Smooth.
*Fruit skin*.—Flavor — Considered mild to neutral.
*Fruit skin*.—Color — Red and Carmine over Green (Fan #4, Sheet 184-B) at full commercial maturity.
*Fruit skin*.—Lenticels — Few, small, and relatively inconspicuous.
*Fruit skin lenticel color*.—Very Pale Yellow (Fan #1, Sheet 1-D).
*Bloom*.—None.
*Fruit flesh*.—Color — White with a very slight cream tint (Fan #1, Sheet 11-D).
*Fruit flesh*.—Texture — Crisp and considered very juicy.
*Stone cells*.—Generally — Not present.
*Ripening*.—Generally even. Fruit holds well on the tree. Can be harvested in 2-3 pickings.
*Fruit flavor*.—Sweet, balanced, clean; refreshing and mild; very good commercial quality.
*Aroma*.—Light and pleasant.
*Resistance to insects and diseases*.—No particular resistance or susceptibilities were noted. The present variety has not been intentionally tested to expose or detect any susceptibilities or resistances to any known plant and/or other fruit tree disease.
*Hardiness*.—Winter hardiness — hardy. Drought/heat tolerance — tolerant.
*Pollination requirements*.—Pollination is good with many variations nearby; over pollination is typical requiring hand thinning.

We claim:

1. A new and distinct apple tree substantially as described and illustrated herein.

* * * * *